Figure 3:
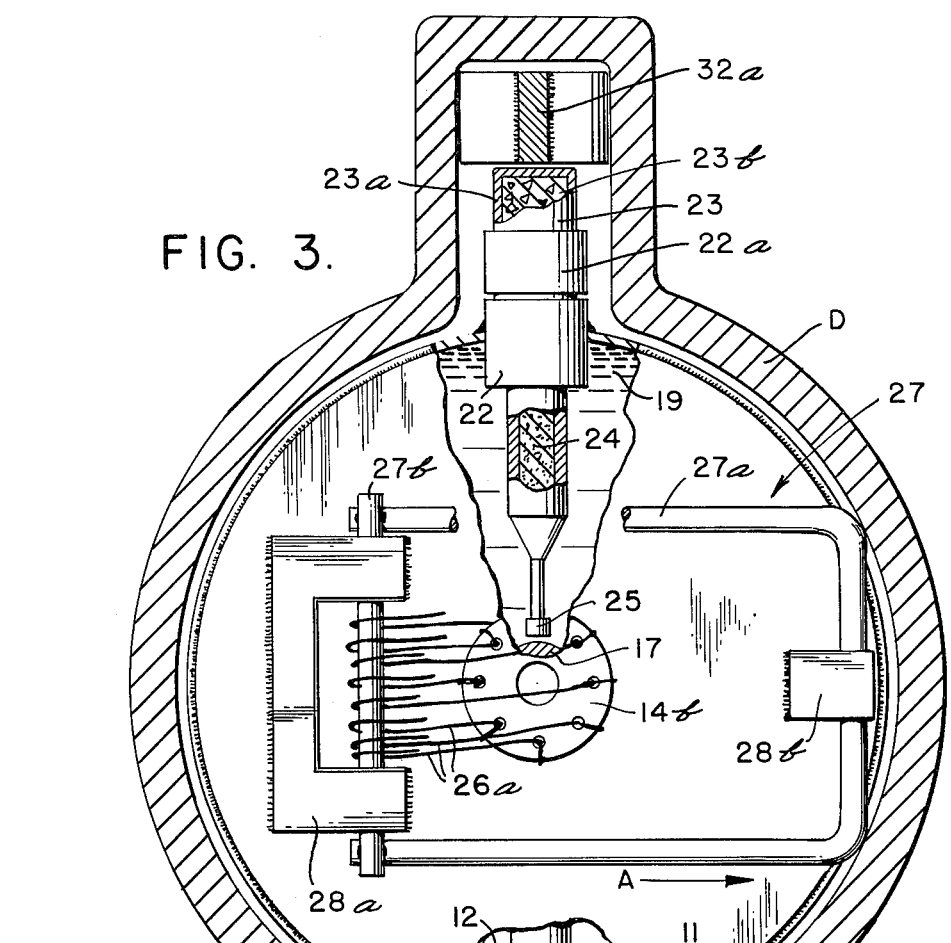

United States Patent [19]

Glass et al.

[11] 3,940,443

[45] Feb. 24, 1976

[54] FUEL-AIR EXPLOSIVE BOMBLET

[75] Inventor: Cecil A. Glass, China Lake, Calif.

[73] Assignee: United States of America as represented by the Secretary of the Navy

[22] Filed: July 14, 1965

[21] Appl. No.: 472,760

[52] U.S. Cl. .......... 102/6, 102/4, 102/7.2, 102/90

[51] Int. Cl.² .................................. F42B 25/12

[58] Field of Search ........... 102/6, 2, 22, 8, 65, 66, 102/90, 7.2, 4

[56] No References Cited

*Primary Examiner* — David H. Brown
*Attorney* — R. S. Sciascia, Roy Miller
*Attorney, Agent, or Firm* — R. S. Sciascia, Roy Miller

EXEMPLARY CLAIM

8. In a device for forming a detonatable fuel-air cloud and effecting a detonation thereof, means including:
   a sealed container;
   a mass of inflammable fuel substantially filling said container;
   a plurality of actuatable detonators fixed to said containers;
   a detonatable burster charge mounted within said container and surrounded by said fuel adapted to be selectively detonated for thereby establishing an outwardly directed shock wave of a magnitude sufficient for rupturing said container, dividing said mass into a plurality of smaller masses and rapidly propelling said masses and said detonators outwardly from said containers through ambient atmospheric air, whereby a detonatable cloud of a fuel and air mixture may be thus established with said detonators being caused to pass therethrough; and
   means connected with said detonators adapted to actuate said detonators as they pass through the cloud, whereby said cloud may be detonated in response to an actuation of the detonators.

8 Claims, 4 Drawing Figures

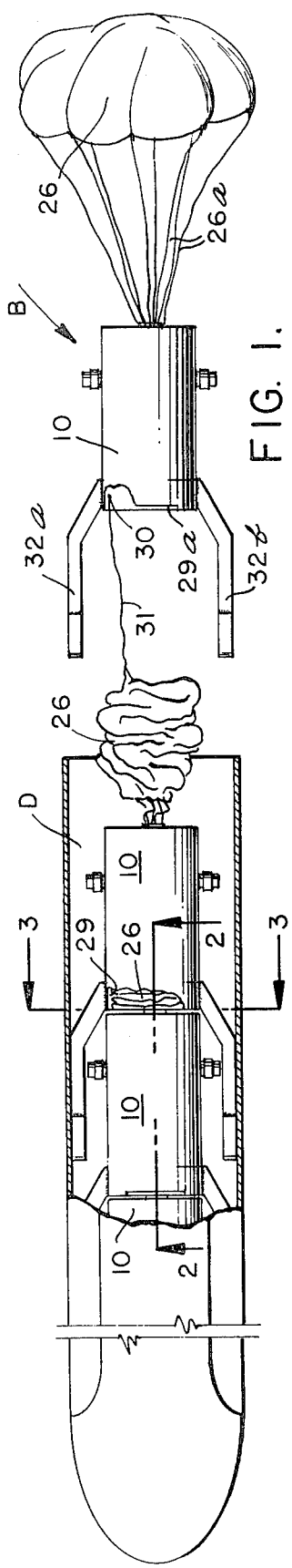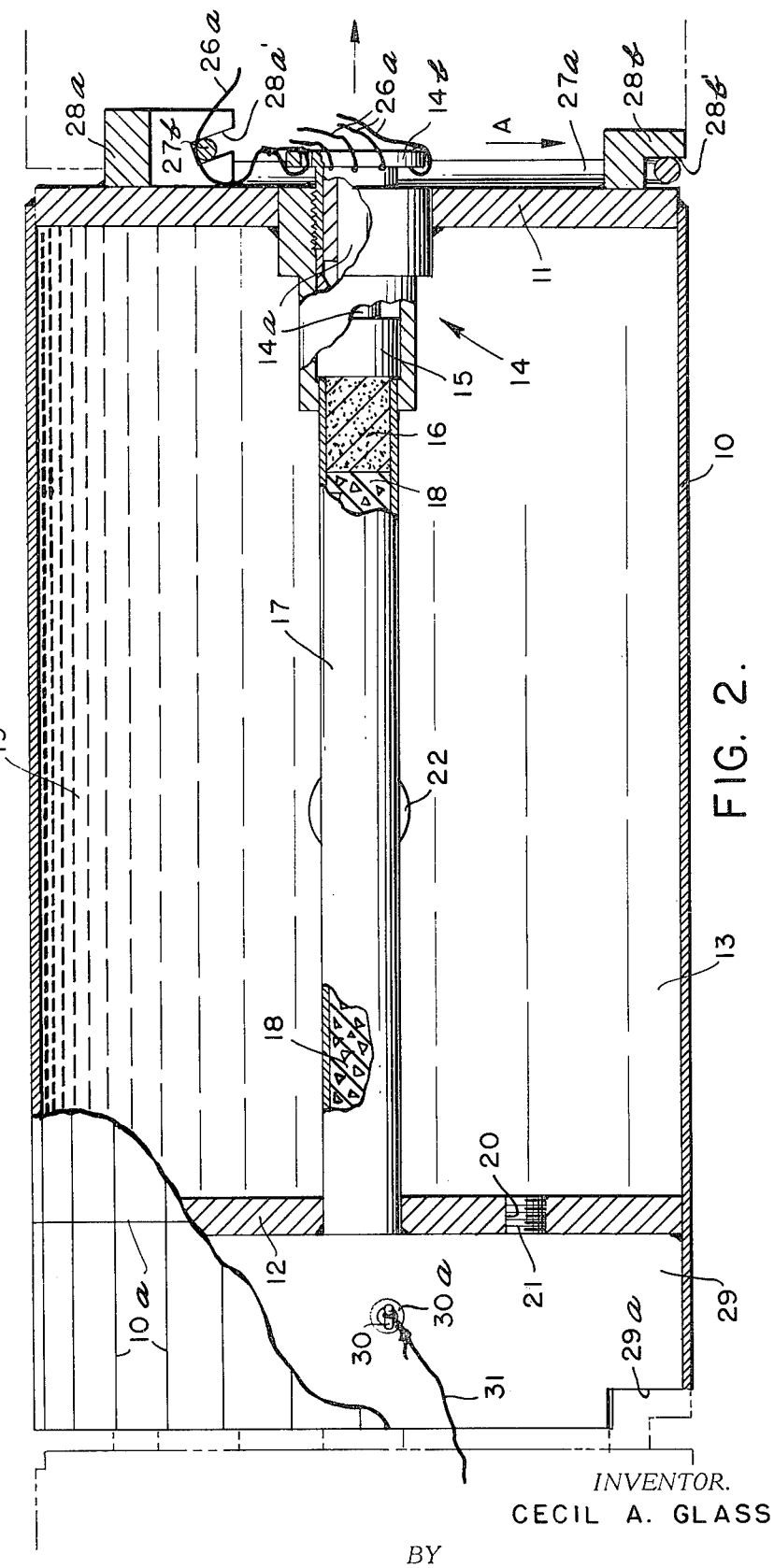

INVENTOR.
CECIL A. GLASS
BY
P.H. Fisht
ATTORNEY.

FUEL-AIR EXPLOSIVE BOMBLET

The invention described herein may be manufactured and used by or for the Government of the United States of America for governmental purposes without the payment of any royalties thereon or therefor.

The present invention relates generally to concussion-type or blast weapons, and more particularly to a fuel-air explosive (FAX) bomblet for establishing and subsequently detonating a fuel-air cloud at ground level, whereby large target areas may be effectively subjected to the damaging overpressure effects of a detonation velocity or shock wave generated through the detonation of the fuel-air cloud.

The destructuve characteristics of detonation waves are well-known, consequently the desirability of concussion-type weapons, today, is a recognized fact. Concusion-type weapons have a variety of uses, including defoliation of botanical growth and destruction of vehicles and structures, as well as in overcoming enemy personnel. However, where large unconfined targets areas must be subjected to overpressure, established through the detonation of an explosive device, or enemy troops have "dug-in" into remote fox holes, caves, and the like, conventional weapons of the type which capitalize on blast effects are normally rendered ineffective, due, in part, to the rate at which an established detonation velocity will decay when projected from a distance.

Therefore, the purpose of the instant invention is to provide a practical weapon which is capable of subjecting large target areas to the effects of detonation established shock waves. This is accomplished, generally speaking, by providing means for establishing a large fuel-air cloud, i.e., a cloud formed of a mixture of atomized fuel and air, of a "pancake" configuration over a selected target area, and for subsequently detonating the thus established cloud, whereby detonation waves or shock waves thus established may be utilized for producing devastating effects throughout a selected target area, including bunkers, caves, fox holes, building and the like located therewithin.

An object of the instant invention is to provide a practical device capable of establishing a large fuel-air cloud and, subsequently, effecting a detonation thereof.

Another object is to provide blast weapons which may be effectively delivered from airborne vehicles to inaccessible target areas for destroying targets disposed therewithin.

Still another object is to provide simple and practical concussion-type weapons, which may be effectively ejected and delivered in large numbers from aircraft, armed during descent, and activated slightly above the surface of the ground for effectively establishing and detonating a large pancake-shaped fuel-air cloud extending along the surface of the target area.

Figure 4:
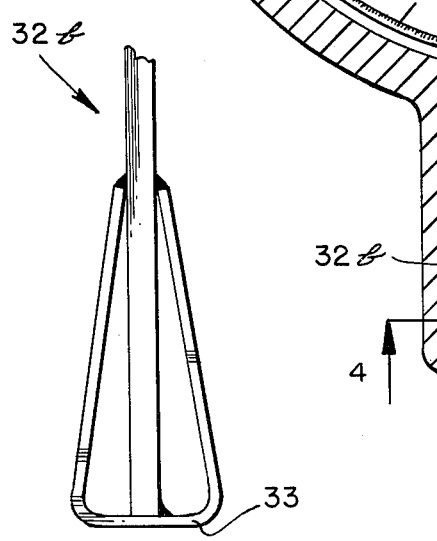

Other objects, advantages and novel features of the invention will become apparent from the following detailed description of the invention when considered in conjunction with the accompanying drawings wherein:

FIG. 1 comprises a partially sectioned, operational schematic view of a launcher, of a type normally transported by airborne aircraft, having arranged therewithin a plurality of similar bomblets of the instant invention;

FIG. 2 comprises a cross sectional view of one of the bomblets of FIG. 1, taken generally along lines 2–2 of FIG. 1;

FIG. 3 comprises an end view of one of the bomblets of the instant invention, taken generally along lines 3–3 of FIG. 1; and FIG. 4 comprises a detail view of one of the legs of the device, taken along lines 4–4 of FIG. 3.

Referring now to the drawings, wherein like reference characters designate like or corresponding parts throughout the several views, there is shown in FIG. 1 a bomblet dispenser or launcher D of a type which may be secured beneath a transporting aircraft for delivering the bomblets of the instant invention, generally designated B. The dispenser or launcher D is normally provided with suitable means, not shown, for mating it with a transporting aircraft, also not shown, and for initiating a launching of the bomblets B therefrom. Such devices are well-known, hence a detailed description of the launcher D is moitted in the interest of brevity. However, it will be appreciated that the launcher D must have cross-section dimensions and be of a suitable configuration for retaining and subsequently dispensing or launching the bomblets B.

Each bomblet B includes a shell of an elongated tubular configuration having a tubular side wall 10, and a pair of transverse end walls 11 and 12 welded to the wall 10, FIG. 2, for defining therebetween a sealed chamber 13. The side wall 10 is provided with a plurality of parallel score lines 10a extending the length thereof. These score lines serve to weaken the wall 10 so that it is caused to uniformly rupture and fragment in response to detonation or shock waves generated within the chamber 13, whereby the contents of the chamber may be propelled outwardly, in radial directions, to form a substantially symmetrical fuel-air cloud.

Mounted to extend through the end wall 11 there is an air-arming, impact-firing fuze 14. The fuze 14 may be of any one of several known types of fuzes which are provided with a reciprocating, fuze-actuating rod or plunger 14a operatively connected through a suitable linkage to a fuze arming and firing device 15.

The device 15 includes a suitable escapement mechanism of a known type which causes the fuze 14 to arm, by permitting a firing train to be displaced and brought into alignment therewithin, once the rod 14a is pulled or partially extracted from the fuze 14, and and will activate once the rod 14a is again inserted into the fuze 14 for thus effecting a firing thereof. Such devices are well-known, hence a detailed description thereof is omitted in the interest of brevity. Coupled in an operative relationship with the device 15 is a booster charge 16, i.e., an explosive device which is to be initiated in response to a firing of the firing train within the fuze 14. This charge may be formed to any suitable explosive material of a type which is readily detonated for initiating a detonation of an associated burster charge.

A tubular walled container or burster tube 17 extends from a point adjacent the device 15 to the opposite end wall 12 of the bomblet B and is secured therebetween by any suitable means. The burster tube 17 serves to house the booster charge 16 and further contains a suitable burster charge 18 aligned in operative communication therewith. The charge 18 is formed of any suitable high-order explosive material of a type which will detonate in response to a detonation of the booster charge 16. Conventional burster charges, such as those commonly referred to as an "Aplex Explosive Stick", and tetryl pellets, for example, have been found to function satisfactorily.

Surrounding the burster tube 17 is a liquid fuel 19 of a suitable type which may be detonated when atomized, partially vaporized and mixed with air. Ethylene oxide has been found to function quite satisfactorily for this purpose. The plate 12 is provided with a threaded opening 20 through which the liquid fuel 19 may be introduced into the chamber 13 and is operatively sealed by means of a suitable threaded plug 21.

Mounted in diametric opposition along the wall 10 of the bomblet B, there is a pair of "pyro-delay" devices 22. Each device 22 extends from its innermost end, which is located at a point adjacent the burster tube 17, through the wall 10 and terminates at its outermost end disposed outside the chamber 13. The outermost end of each "pyro-delay" is provided with a suitable coupling means 22a, which serves to securely couple thereto a cloud detonator 23. Each of the cloud detonators 23 comprises a cup-shaped container 23a filled with a suitable high-order explosive device 23b, such as tetryl pellet, for example.

Each of the cloud detonators 23 are detonated in response to a delayed firing of the "pyro-delay" devices 22. Each of the "pyro-delay" devices is filled with a slow-burning pyrotechnic composition 24, of a type which requires a significant burning period before it is consumed, for effecting a detonation of the detonator 23. The innermost end of each of the devices 22 is sealed by means of a thin metal cup 25, which may be imploded when the adjacent burster charge 18 is exploded, for effecting an initiation of the composition 24.

In view of the foregoing, it will be appreciated that a desired fuel-air cloud may be established in response to a firing of the arming and firing mechanism of the device 15. That is to say, when the device 15 is fired, the booster charge 16 is detonated in response thereto for thereby cuasing a chock wave to be projected through the explosive material of the burster charge 18. This shock or detonation wave initiates a detonation of the explosive material of the burster charge 18 which then projects shock or detonation waves through the fuel 19. As the shock wave is propagated, an initiation of the "pyro-delay" is effected and the wall 10 is caused to rupture along the score lines 11, and, as a practical matter, to subsequently disintegrate in response to the propagated shock wave. The shock wave is permitted to travel outward from the ruptured wall 10 in a radial directions, rather than in random directions. Since the shock wave continues to travel outwardly through the wall 10, it serves to propel the fuel 19 and the initiated "pyro-delay" devices 22 outwardly and away from the bomblet B. As the fuel 19 is acted upon by the shock wave and propelled through ambient atmosphere, it is thereupon caused to assume an atomized state and become thoroughly mixed with ambient air. Consequently, a highly explosive fuel-air cloud, of a pancake configuration, is rapidly established near the ground or the surface of the target area.

It has been found that formation of the fuel-air cloud will occur in a relatively short period of time, i.e., withiin a few milliseconds. Therefore, the "pyro-delay" devices 22 may be of a type which effect a detonation of the coupled detonators 23 while the detonators are suspended in motion within the thus formed cloud. In response to a detonation of the detonators 23, a detonation velocity or shock wave is established and caused to pass into and effect a detonation of the fuel-air cloud. Detonation of the fuel-air cloud serves to establish a detonation velocity or shock wave, whereby a destructive overpressure within the target area is achieved as a consequence of the thus established detonation velocity being passed through the target area.

The following example serves to illustrate the effectiveness of the bomblet B. A vertically aligned chamber defined by thin, vertically scored aluminum walls, was filled with a 10-3/4 pound charge of ethylene oxide liquid fuel. A one-fifth pound "Aplex stick" burster charge was detonated within the chamber. A resulting horizontally disposed, substantially symmetrical cloud, having horizontal dimensions of approximately 20' × 30' and a thickness of 2 feet was established within 40 milliseconds. At the termination of a 40 millisecond delay period, the cloud was detonated by "pyro-delay" devices, of the type hereinbefore described. A detonation velocity of approximately 1500 meters per second was established, resulting in an overpressure of approximately 200 p.s.i. throughout the area previously occupied by the cloud. The duration of the thus established overpressure was approximately 2.5 to 3 milliseconds, which is deemed sufficient for combat purposes.

As indicated in FIG. 1, the bomblets B are to be supported in descent by means of conventional devices or parachutes 26. A parachute 26 is attached to the fuze 14 of each bomblet B by means of shroud lines 26a secured to a coupling or bracket 14b formed at the outermost end of the actuating rod 14a. The shroud lines 26a further serve to partially withdraw the rod 14a from the fuze 14, as the bomblet B descends, for thereby initiating an arming of the fuze 14, through an activation of the fuze-arming mechanism 15.

In order to preclude an accidental arming of the fuze 14, while the bomblets B are confined within the launcher D, a safety device 27, FIG. 3, is provided for preventing an unfortuitous partial extraction of rod 14a. The device 27 includes a member 27a, of a generally U-shaped configuration, and a bar 27b welded across the opening of the "U", FIG. 3. A set of brackets 28a and 28b are mounted on the end wall 11 of the bomblet B, at opposite sides of the fuze 14, and are so formed and aligned as to provide a plurality of mutually spaced, horizontally aligned slots 28a' and 28b' faced in a comman lateral direction, so that the opposite ends of the device 27 may be slidingly received and restrained therein. It is intended that the device 27 be inserted and extracted from the brackets 28a, 28b by sliding the device 27 in a transverse direction across the end of the bomblet B, with the bar 27b being directed toward the slot 28a'. It will therefore be appreciated that the device 27 is operatively seated within the slots 28a' and 28b' and is restrained against desplacement in a longitudinal direction thereby.

At the time of assembly, the shrouds 26a are manually drawn to one side of the bomblet B, adjacent the bracket 28a, while the device 27 is being secured to the bomblet by being inserted into the slots 28a' and 28b', in the aforedescribed manner. As the device 27 is thus being secured to the bomblet, the bar 27b is brought into an abutting relationship with the shrouds 26a. The shrouds 26a may now be retained, by the device 27, in a manner such that in the event forces of tension are applied, in a longitudinal direction, to the shrouds 26a, the shrouds will act to apply a transversely directed force component to the coupling 14b, and a diagonally directed force component to the device 27. Where the device 27 is free, or its displacement is unobstructed, the diagonally directed force component will serve to push or extract the device 27 from the slots of brackets 28a and 28b. Once the device 27 is thus displaced, the shrouds 26a are permitted to move over-center, and become longitudinally aligned with the fuze 14, so that the applied tension now may be utilized for partially extracting or displacing the rod 14a from the fuze 14, whereby the device 15 may become activated for thereby causing the fuze 14 to assume an armed condition.

In order to provide a safe transport of the bomblets B, each device 27 and the internal surfaces of the dispenser or launcher D are so dimensioned as to retain the device 27 against transverse displacement from the slots 28a' and 28b' of the brackets 28a and 28b through an abutting engagement established therebetween, as illustrated in FIG. 3. Hence, each fuze 14, when disposed within the launcher D, will be prevented from arming so long as the associated bomblet B is retained by the dispenser D.

Turning now to FIGS. 1 and 2, it will be noted that the end wall 12 of each of the bomblets B is displaced inwardly from the adjacent end of the wall 10 so that a vacant, open-end cavity 29, defined by walls 10 and 12, is established within one end of the bomblet B. Each cavity 29 serves as a housing or storage means for storing a parachute 26 for an adjacent bomblet B so that the bomblets B may be "nested" within the dispenser or launcher D, as illustrated in FIG. 1. It is to be noted that a cutaway portion or slot 29a is formed within the wall 10, near the outermost end of the cavity 29. This slot accommodates a passage therethrough of the device 27 mounted on the adjacent bomblet B, so that it may be brought into an abutting relationship with the internal surface of the dispenser D and retained within the slots of the brackets 28a and 28b, associated therewith as aforedescribed.

Mounted within each cavity 29 is static line anchor post 30 through which a static-line 31 of the parachute 26 of the adjacent bomblet may be secured. The post 30 may be inserted through the wall 10 and retained in place by a conventional rubber grommet 30a mounted in a suitable opening extending through the wall 10. It is to be understood that the post 30 is so shaped at its outermost end as to preclude a passage thereof through the opening into the cavity 29. However, for the sake of convenience in "nesting" the bomblets, it is desirable to form the grommet 30a in a manner such that the innermost end of the post 30 may be inserted therethrough after the static-line 31 is attached thereto.

Each bomblet B is further provided with a standoff device comprising at least one pair of oppositely disposed legs 32a and 32b secured to the outermost surface of the wall 10 and aligned to extend downwardly from the bomblet B as it descends, whereby the bomblet may be supported by the parachute 26 during descent and by the legs 32a and 32b at impact. It will therefore be appreciated that the legs 32a and 32b will impact at the surface of the target area, so that detonation of the burster charge 18 may be effected while the bomblet is supported thereby at a preselected distance above the target area. Consequently, small surface objects will not impede the formation of a fuel-air cloud. Where desired, a platelike member 33, FIG. 4, may be faced downwardly and secured across the lowermost end of the legs 32a and 32b for increasing the surface of the legs at the points of impact, in order to reduce penetration of the ends of the legs into the surface of the target area.

In summary, the bomblets B may be "nested" within a launcher D by attaching the shrouds 26a of the parachutes 26 to the brackets or couplings 14b of the fuzes 14, and attaching static-lines 31 to the anchor posts 30 of each succeeding bomblet B and inserting the bomblets into the launcher D with the parachutes 26 being aligned to face aft. The launcher D is now sealed at its aft end by any suitable releasable means, not shown, which may be discarded for opening the launcher D on command.

When the bomblets B are to be launched from above the target area, the aft end of the launcher D is opened on command. The aft or last-in-line parachute 26 is now subjected to an existing airstream, whereby it is caused to be discharged from the launcher D and opened by the imposed effects of the airstream. As a consequence of the opening of the parachute 26, the airstream causes the parachute 26 to act against and withdraw the attached last-in-line bomblet B by applying tension to the shroud lines 26a. As the last-in-line bomblet B is withdrawn from the launcher, the attached static-line 30 serves to withdraw the parachute 26 of the next-in-line bomblet B from the launcher D. However, as the shroud lines 26a are drawn taut on the next-in-line bomblet B, the static-line 30 will be caused to part as a consequence of the applied tension, whereby the last-in-line bomblet B will be allowed to descend, supported only by the parachute 26 attached thereto. It is to be understood that by the time the static-line 30 is caused to part the parachute 26 of the next-in-line bomblet will have been displaced sufficiently for being subjected to the existing airstream, whereupon the next-in-line bomblet B may be withdrawn. This process is then repeated until all bomblets B have been launched or dispensed from the launcher or dispenser D and separated for individual descent.

Once a given bomblet B is drawn from the launcher D, the safety device 27 is freed for displacement from the slots 28a' and 28b'. The tension applied to the shroud lines 26a causes the shroud lines to act against the rod 27b for forcing the device 27 in a transverse direction, indicated by arrow A, FIGS. 2 and 3, whereupon the device 27 is extracted from the slots of the brackets 28a and 28b and permitted to fall away from the bomblet B. Once the device 27 is extracted from the slots of the brackets, the shroud lines 26a apply tension, in a longitudinal direction, to the rod 14a causing it to be partially extracted from the fuze 14. As a result of this displacement, the mechanism 15 will effect an arming of the fuze 14. Once the legs 32a and 32b impact at the surface of a selected target area, the rod 14a is driven, through forces of inertia, back into the fuze 14, whereupon the firing train of the device 15 is initiated. In response to an initiation of the firing train, the booster charge 16 functions to detonate the burster charge 18. As the burster charge is detonated, a detonation wave is projected through the fluid 19 and wall 10 causing the wall 10 to rupture along score lines 10a and fragment, with the fluid 19 and wall fragments being driven outwardly in radial directions about the bomblet. The projected detonation wave, or shock wave, also serves to initiate the "pyro-delay" devices 22, which are subsequently driven from the bomblet. The fluid 19 becomes atomized into fine particles which are caused to mix with ambient air whereby a resulting fuel-air cloud comprising fine droplets of fuel, air and fuel vapor, is established.

Upon establishment of the fuel-air cloud, the "pyro-delay" devices 22 detonate the cloud detonators 23 which, in turn, serve to detonate the established fuel-air cloud. In practice, this cloud is formed and detonated within approximately 40 milliseconds. As the thus established cloud is detonated, its detonation velocity, or shock wave establishes a lethal overpressure within the area previously occupied by the cloud, as well as immediately adjacent areas, such as buildings, caves and the like, for example.

In view of the foregoin, it will be appreciated that the present invention provides a simple, economic and effective device, which may be utilized as an effective blast weapon against targets located within large unconfined target areas, as well as targets situated in buildings, caves, bunkers, depressions and the like disposed adjacent the surface of selected target areas.

Obviously many modifications and variations of the present invention are possible in the light of the above teachings. It is therefore to be understood that within the scope of the appended claims the invention may be practiced otherwise than as specifically described.

What is claimed is:

1. In a bomblet for establishing and detonating a substantially flat horizontally disposed fuel-air cloud along the surface of a selected target area;
    a hermetically sealed, elongated shell having longitudinal score lines extending the length thereof;
    an inflammable liquid substantially filling said shell;
    an elongated burster charge disposed within said shell in concentric alignment therewith adapted to be detonated to thereby generate detonation waves for rupturing said shell along said score lines and rapidly propelling the liquid radially from said shell through ambient atmosphere, whereby said inflammable liquid is caused to atomize, partially vaporize and mix with air to thus form a substantially flat and generally symmetrical cloud of inflammable material extending in radial directions from said shell;
    at least one time-delay detonator including an explosive charge and a time-delay mechanism adapted to be initiated in response to detonation waves projected therethrough and to effect a preselected delayed detonation said explosive charge;
    means mounting said time-delay detonator within said shell in a manner such that detonation waves generated through a detonation of said burster charge may be caused to impinge thereon for causing said detonator to be initiated and propelled outwardly into the cloud of inflammable liquid as it is being formed, whereby a subsequent detonation of said cloud may be effected through a delayed detonation of said explosive charge; and
    fuze and booster means coupled with said burster charge for effecting a detonation thereof.

2. The combination of claim 1, further characterized in that said time-delay mechanism includes:
    a train of pyrotechnic means of a type requiring a preselected time period for establishing a completed burning thereof.

3. The combination of claim 2, further comprising:
    standoff means fixed to said shell adapted to engage the surface of a selected target area and to maintain said shell in displaced relationship therewith.

4. The combination of claim 3, further characterized that said fuze and booster means includes:
    an air-arming and impact-firing device fixed to said shell and adapted to be actuated for effecting an arming and subsequent firing thereof, whereby the bomblet may be ejected from an airborne vehicle and the fuze actuated during descent and further actuated on impact with the surface of the target area for causing said burster charge to be detonated.

5. The combination of claim 4 further including:
    a parachute coupled with said fuze adapted to retard descent of the bomblet and to actuate said fuze for thereby effecting an arming of said fuze as the bomblet is caused to descent subsequent to an ejection thereof from an airborne vehicle.

6. The combination of claim 5, further including:
    a line secured said shell adapted to be coupled with a parachute of a given other bomblet, whereby a plurality of bomblets may be coupled together and delivered by mass-delivery techniques, for thereby insuring an ejection thereof from an airborne vehicle.

7. The combination of claim 5, further including:
    a safe-arming device operatively coupled with said fuze, whereby an arming actuation of said fuze may be prevented until said bomblet has been ejected from an airborne vehicle.

8. In a device for forming a detonatable fuel-air cloud and effecting a detonation thereof, means including:
    a sealed container;
    a mass of inflammable fuel substantially filling said container;
    a plurality of actuatable detonators fixed to said containers;
    a detonatable burster charge mounted within said container and surrounded by said fuel adapted to be selectively detonated for thereby establishing an outwardly directed shock wave of a magnitude sufficient for rupturing said container, dividing said mass into a plurality of smaller masses and rapidly propelling said masses and said detonators outwardly from said containers through ambient atmospheric air, whereby a detonatable cloud of a fuel and air mixture may be thus established with said detonators being caused to pass therethrough; and means connected with said detonators adapted to actuate said detonators as they pass through the cloud, whereby said cloud may be detonated in response to an actuation of the detonators.

9. Each and every novel feature and combination of novel features presented in or possessed by the invention herein disclosed.

* * * * *